United States Patent
Jolly et al.

(10) Patent No.: US 8,112,161 B2
(45) Date of Patent: Feb. 7, 2012

(54) IMPLANTABLE ELECTRODE WITH VARIABLE MECHANICAL MODULATION WIRING

(75) Inventors: Claude Jolly, Innsbruck (AT); Stefan Nielsen, Innsbruck (AT); Fabrice Béal, Mutters (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

(21) Appl. No.: 12/700,988

(22) Filed: Feb. 5, 2010

(65) Prior Publication Data

US 2010/0204768 A1    Aug. 12, 2010

Related U.S. Application Data

(60) Provisional application No. 61/150,496, filed on Feb. 6, 2009.

(51) Int. Cl.
*A61N 1/05*    (2006.01)
(52) U.S. Cl. ............. 607/137; 607/136; 607/55; 607/57
(58) Field of Classification Search ............. 607/45–46, 607/136–137, 55–57; 600/25
See application file for complete search history.

(56) References Cited

U.S. PATENT DOCUMENTS

| | | | |
|---|---|---|---|
| 2001/0027342 A1* | 10/2001 | Dormer | 623/10 |
| 2004/0127968 A1 | 7/2004 | Kuzma et al. | 607/137 |
| 2006/0206185 A1* | 9/2006 | Schuller | 607/137 |
| 2006/0264897 A1* | 11/2006 | Lobl et al. | 604/506 |
| 2007/0088335 A1 | 4/2007 | Jolly | 604/891.1 |
| 2007/0150039 A1* | 6/2007 | Leigh et al. | 607/152 |
| 2010/0305676 A1* | 12/2010 | Dadd et al. | 607/137 |

FOREIGN PATENT DOCUMENTS

| | | |
|---|---|---|
| AU | 2004240231 | 1/2005 |
| WO | WO 2008/042863 | 4/2008 |
| WO | WO 2010/091237 | 8/2010 |

OTHER PUBLICATIONS

International Searching Authority, *Written Opinion*—International Application No. PCT/US2010/023298.
International Searching Authority, Invitation to Pay Additional Fees and, Where Applicable, Protest Fee—International Application No. PCT/US2010/023298, dated Aug. 6, 2010, 4 pages.

* cited by examiner

*Primary Examiner* — Carl H Layno
*Assistant Examiner* — Paula J Stice
(74) *Attorney, Agent, or Firm* — Sunstein Kann Murphy & Timbers LLP

(57) ABSTRACT

A cochlear implant electrode is described. A basal electrode lead carries electrical stimulation signals from an implant housing to a cochleostomy opening, and a portion of the electrode lead has a periodically recurring lead shape. An apical electrode array at the cochleostomy end of the electrode lead passes into a cochlea scala and includes electrode contacts for applying the electrical stimulation signals to target neural tissue. A portion of the electrode array has a periodically recurring array shape different from the lead shape.

15 Claims, 5 Drawing Sheets

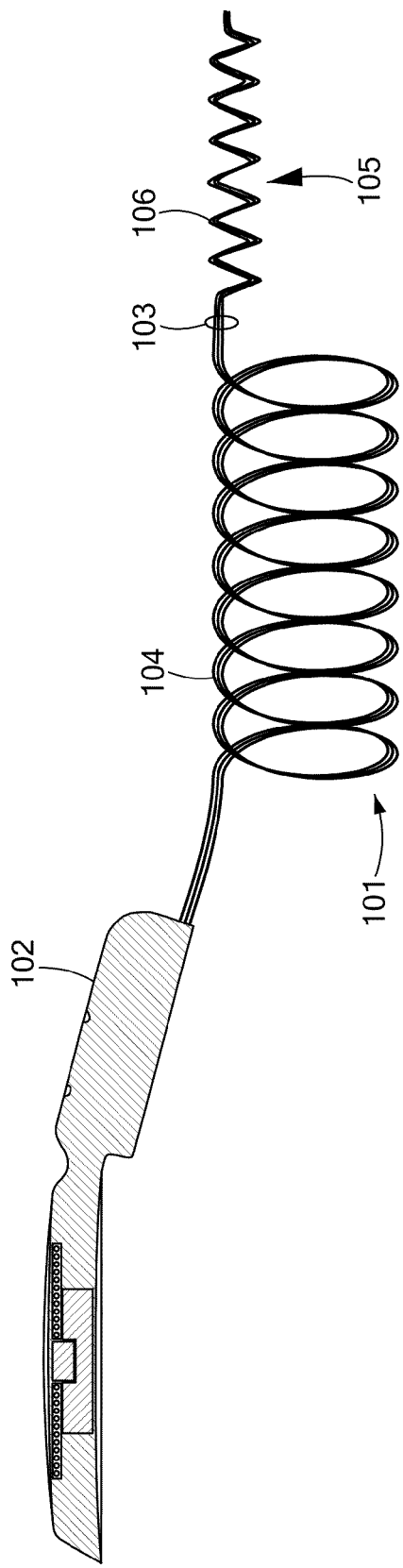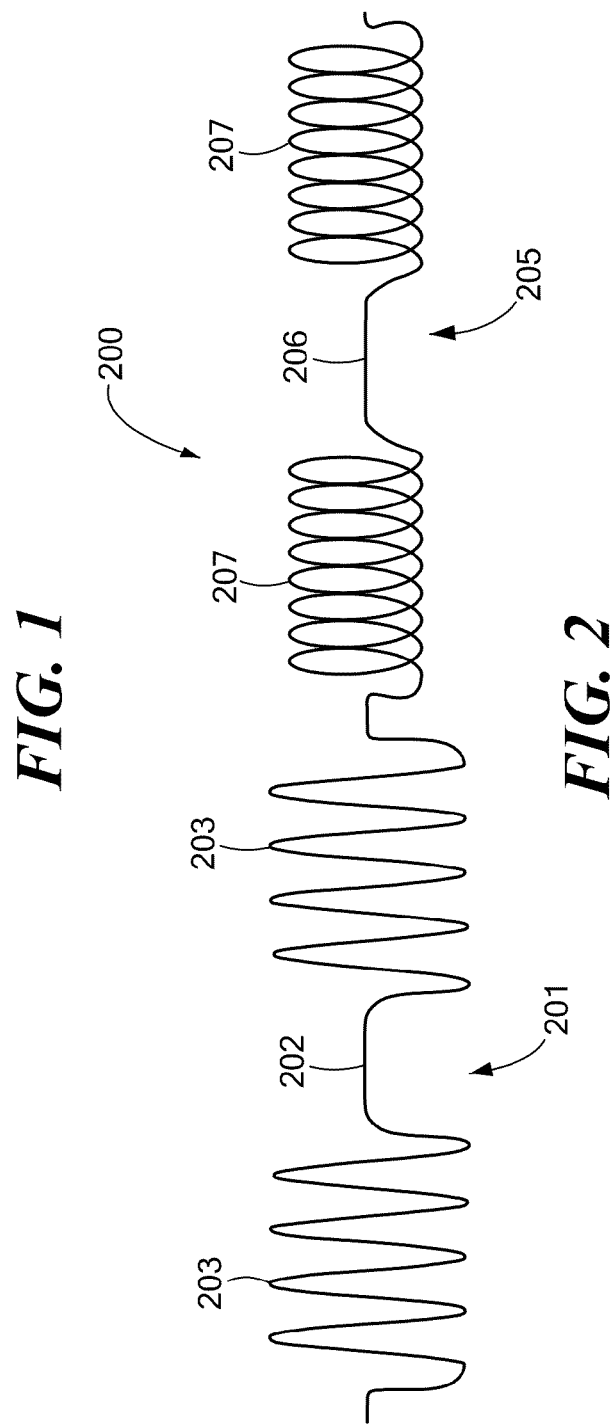
FIG. 1
FIG. 2

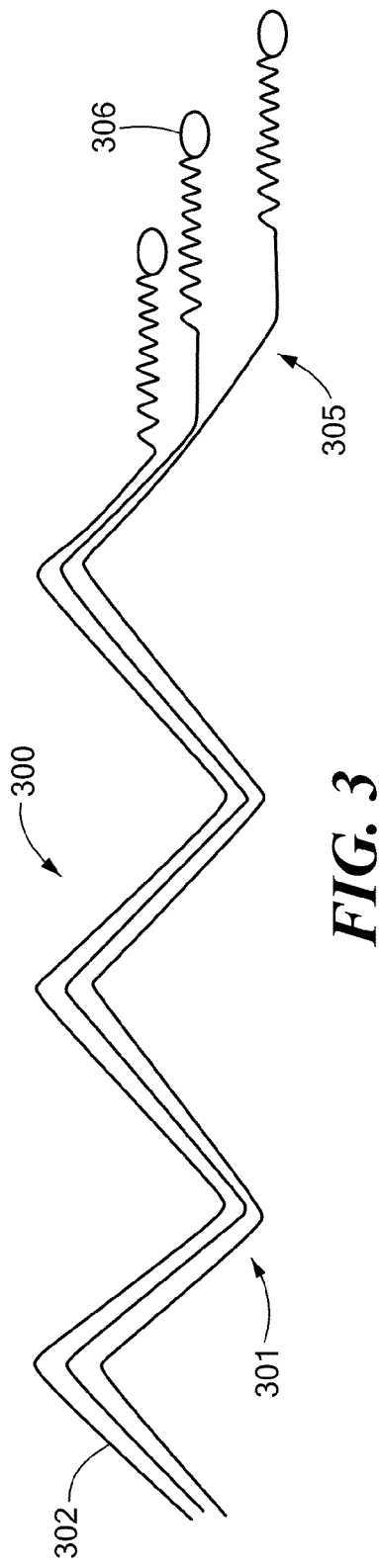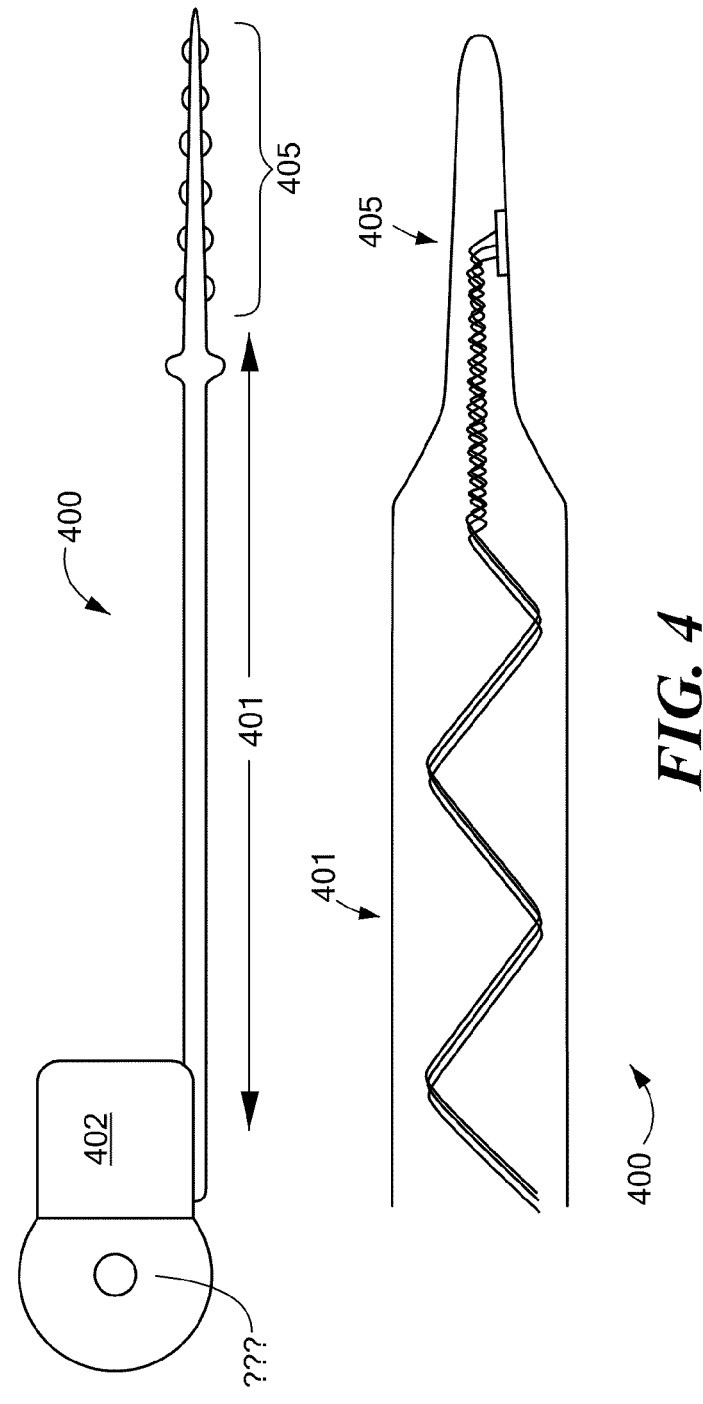

IMPLANTABLE ELECTRODE WITH VARIABLE MECHANICAL MODULATION WIRING

This application claims priority from U.S. Provisional Patent Application 61/150,496, filed Feb. 6, 2009; incorporated herein by reference.

FIELD OF THE INVENTION

The present invention relates to medical implants, and more specifically to a stimulation electrode used in cochlear implant systems.

BACKGROUND ART

Implantable multi-channel electrodes for neuro-stimulation or neuro-modulation need to be mechanically robust, and yet flexible and of small size to be inserted into body cavities such as the human cochlea, or to be inserted into a body organ such as the brain. Typically, the wires in most implant electrodes have a homogenous shape from one end to the other: either generally straight, repeating coiled loops, or recurring wave shapes. In environments where the implanted electrodes continuously move relative to the surrounding tissues, matching the mechanical properties of the electrodes to the properties of the surrounding tissues is important for avoiding adverse biological reactions and massive scar tissue generation.

Implant electrodes are being developed for insertion ever more deeply into body cavities of progressively more complex shape. So an implant electrode should have non-uniform and non-homogeneous mechanical properties (e.g., bending and flexing) to accommodate the tortuous path that it must take, and also for maintaining biological compatibility with the surrounding tissue. There may be some parts of an implant electrode that need to be highly resistant to micro-movement (e.g., the portion of a cochlear implant electrode which lies immediately under the skin on the skull). Other portions of the implant electrode may need to be very bendable to accommodate a convoluted insertion path (e.g., the portion of a cochlear implant electrode that goes into the cochlea). Some portions of the implant electrode may be exposed to occasional impact force and so may need to be very resistant to external impact (e.g., portions of a cochlear implant electrode under the skin on the skull).

Some compromise in these factors must be achieved in circumstances where high flexibility is needed but space is very limited (e.g. as in the cochlea). Electrode structures that are highly resistant to micro-movements tend to occupy relatively more space, whereas electrode structures that are small in size tend to be relatively rigid. Presently, as the number of electrode stimulation channels increases, the number of corresponding metallic wires in the electrodes also increases. That in turn causes the implant electrodes to become increasingly rigid.

As used herein, the term "electrode array" refers to the apical end section of the implant electrode that penetrates into a cochlea scala of the inner ear. An electrode array has multiple electrode contacts on or slightly recessed below its outer surface for applying one or more electrical stimulation signals to target audio neural tissue. An "electrode lead" refers to the basal portion of the implant electrode that goes from the implant housing to the electrode array. It usually has no contacts except perhaps a ground electrode and it encloses connecting wires delivering the electrical stimulation signals to the electrode contacts on the electrode array. The term "electrode" refers to the entire implant electrode from end to end, that is, the combination of the electrode array and the electrode lead.

SUMMARY OF THE INVENTION

Embodiments of the present invention are directed to a cochlear implant electrode. An extra-cochlear electrode lead contains electrode wires for carrying electrical stimulation signals from an implant housing to a cochleostomy opening. An intra-cochlear electrode array containing the electrode wires passes from the cochleostomy opening into a cochlea scala and terminates in electrode contacts for applying the electrical stimulation signals to target neural tissue. One or more of the electrode wires in the electrode lead has an associated lead shape and one or more of the electrode wires in the electrode array has an associated array shape which is different from the lead shape. The array shape may differ in amplitude from the lead shape, for example, the lead shape may have a larger amplitude than the array shape. The shapes may include a smoothly varying wave that repeats and/or a sequence of coiled loops.

In some embodiments, the one or more electrode wires in the electrode lead may include a portion without the lead shape, for example, there may be a portion having the lead shape on each side of the portion without the lead shape. Similarly, the one or more electrode wires in the electrode array may include a portion without the array shape, for example, a portion having the array shape on each side of the portion without the array shape. The portion of the one or more electrode wires in the electrode array without the array shape may be rigid for pushing the electrode array into the cochlea scala. The one or more electrode wires in the electrode lead having the lead shape also may include a portion having a different second lead shape that periodically recurs. In addition or alternatively, the one or more electrode wires in the electrode array may have multiple different array shapes.

Some embodiments may also include an impact reinforcement element around a portion of the electrode lead for resisting effects of an external impact. The impact reinforcement element may be a polymer and/or metallic material. The electrode lead or the electrode array may include a portion with an elliptical cross-section. At least one of the shapes may include a smoothly varying wave that repeats and/or a sequence of coiled loops.

Embodiments of the present invention also include a cochlear implant electrode having an extra-cochlear electrode lead containing electrode wires for carrying electrical stimulation signals from an implant housing to a cochleostomy opening. An intra-cochlear electrode array contains the electrode wires and passes from the cochleostomy opening into a cochlea scala and terminates in electrode contacts for applying the electrical stimulation signals to target neural tissue. And an impact reinforcement element surrounds a portion of the electrode lead for resisting effects of an external impact.

In further such specific embodiments, a polymer and/or metallic material may be used for the impact reinforcement element. The impact reinforcement element may form a helical spring shape, for example from round or ribbon wire material. The impact reinforcement element may form a tubular shape and may include a pattern of slits for controlling mechanical properties of the impact reinforcement element. In addition or alternatively, the impact reinforcement element may be embedded in the body of the electrode lead.

BRIEF DESCRIPTION OF THE DRAWINGS

FIG. 1 shows an example of an implant electrode according to one specific embodiment of the present invention.

FIG. 2 shows a portion of another implant electrode according to one embodiment of the present invention.

FIG. 3 shows the principle of another embodiment of an implant electrode.

FIG. 4 shows an example of another implant electrode according to an embodiment of the present invention.

DETAILED DESCRIPTION OF SPECIFIC EMBODIMENTS

Figure 5A:
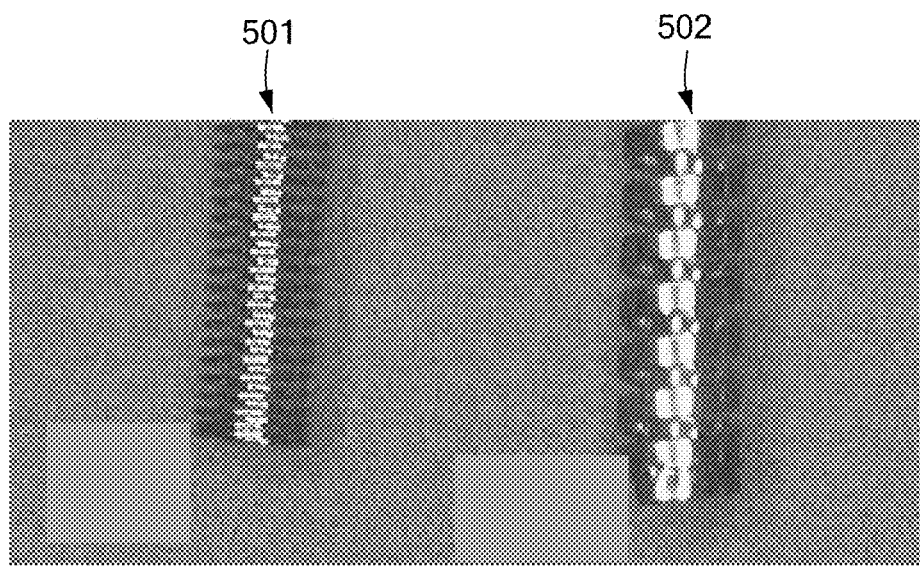
FIG. 5 A-D shows example photographs of impact reinforcement elements in the form of helical springs according to embodiments of the present invention.
Figure 5B:
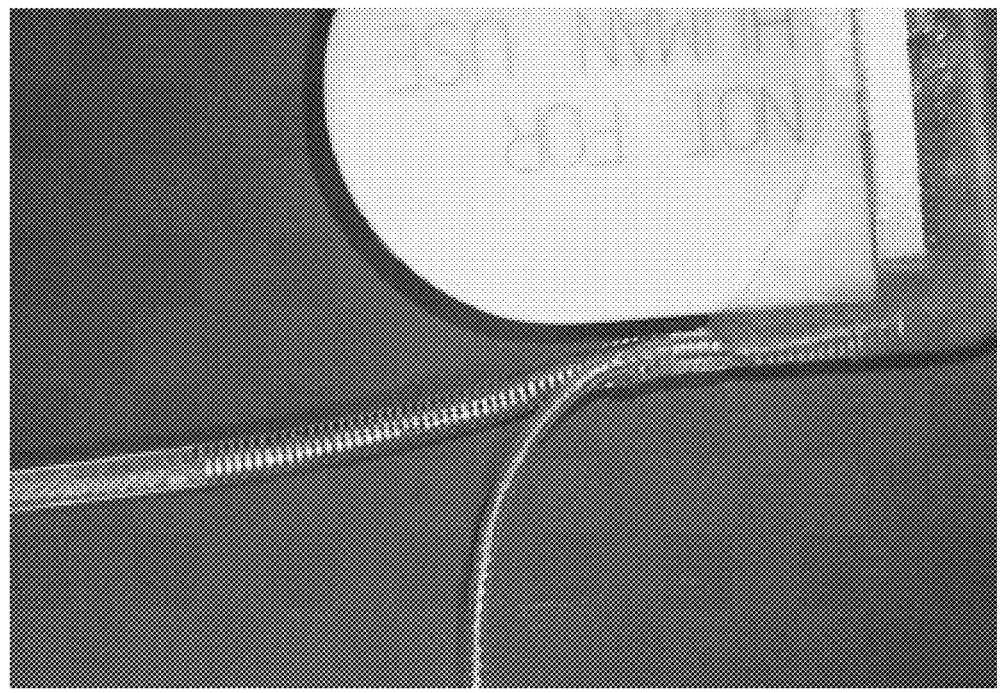
Figure 5C:
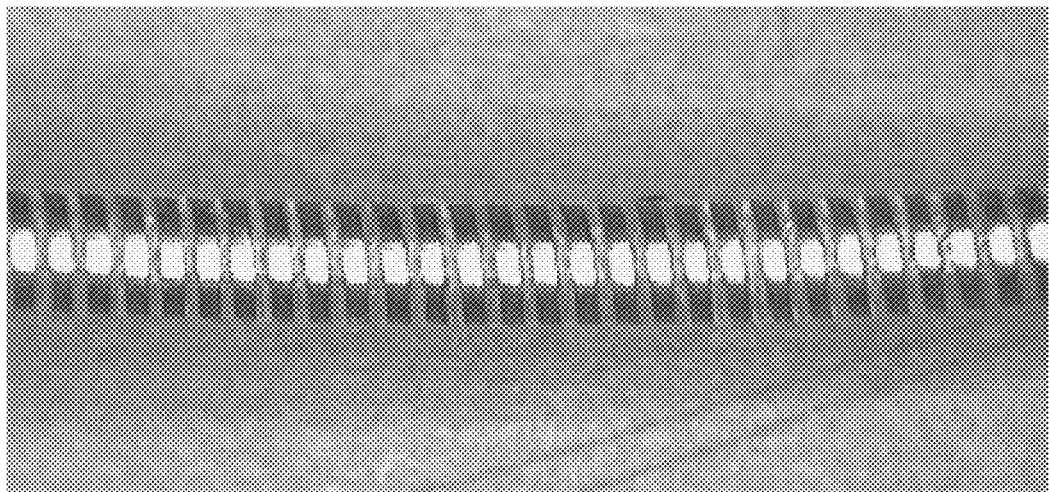
Figure 5D:

Various embodiments of the present invention are directed to an implant electrode that can accommodate the different and potentially contradictory mechanical and physical requirements along its length. Some regions may provide improved resistance to micro-movements, some regions may have improved impact resistance, and other regions may have extra flexibility. The entire implant electrode still satisfies overall limitations such as required size so that it can best accomplish its intended use.

FIG. 1 shows one specific embodiment of an implant electrode 100 having an extra-cochlear electrode lead 101 portion containing multiple electrode wires 104 that carry electrical stimulation signals from an implant housing 102 to a cochleostomy opening 103. An intra-cochlear electrode array 105 portion also contains the electrode wires 104 and passes from the cochleostomy opening 103 into a cochlea scala and terminates in electrode contacts 106 for applying the electrical stimulation signals to target neural tissue. One or more of the electrode wires 104 in the electrode lead 101 portion have an associated lead shape, and one or more of the electrode wires 104 in the electrode array 105 portion have an associated array shape which is different from the lead shape. For example, the array shape in FIG. 1 is a sequence of smoothly varying waves that allow the array to be highly flexible yet having minimum cross-sectional dimensions to aid in atraumatic insertion into the cochlea scala. The lead shape, though, is a series of looped coils that are resistant to micro-movement which can lead to fracture of the electrode wires 104 in the middle ear and on the skull.

Although FIG. 1 shows that all the electrode wires 104 in each portion have the same shape, in other specific embodiments, that may not necessarily be the case, and all the electrode wires 104 may not necessarily have the same shape and structure at the same place. Some electrode wires 104 may be shaped and others not, and in each portion, some electrode wires 104 may have one shape and other electrode wires 104 may have another shape. Some or all of one or more of the electrode wires 104 may have an elliptical cross-section, while other electrode wires 104 may have a circular cross-section. Thus, the shape and size of each individual electrode wire 104 is a subject for individual selection.

FIG. 2 shows a portion of another implant electrode 200 in which the electrode wires in the electrode lead 201 portion include an unshaped lead portion 202 having lead shaped portions 203 on each side. In this case, the lead shaped portions 203 both have the same shape, a large amplitude series of waves which provide resistance to repeated micro-movements or elongation for the section of the electrode lead 201 that is against the skull and/or in the middle ear. In other specific embodiments, the lead shaped portions 203 may have different shapes and/or sizes. Similarly, the electrode wires in the electrode array 205 include an unshaped array portion 206 having array shaped portions 207 on each side. In this case, the array shaped portions 207 both have the same shape, a small sequence of repeating loops which provide maximum flexibility for insertion into the cochlea scala, while the unshaped array portion 206 is rigid for pushing the electrode array 205 into the cochlea scala. In other specific embodiments, the array shaped portions 207 may have different shapes and/or sizes.

FIG. 3 shows the principle of another embodiment of an implant electrode 300. An extra-cochlear electrode lead 301 has multiple electrode wires 302 for carrying electrical stimulation signals from an implant housing to a cochleostomy opening. A lead portion of at least one electrode wire 302 has an associated lead shape, in this case, large recurring triangular waves. An intra-cochlear electrode array 305 at the cochleostomy end of the electrode lead passes into a cochlea scala and includes multiple electrode contacts 306 connected to the electrode wires 301 for applying the electrical stimulation signals to target neural tissue. An array portion of at least one electrode wire 302 has an associated array shape different from the lead shape, in this case, more smaller-size triangular waves.

FIG. 4 shows an example of another embodiment of an implant electrode 400 wherein the natural relaxed state of the electrode is relatively straight, but within a main electrode body made of a resilient silastic material is an electrode lead 401 portion having one or more electrode wires with an associated lead shape (in this case, two large waves that resist micro-movement of the electrode 400), while one or more electrode wires in an electrode array 405 portion has its own associated array shape (in this case, many smaller waves). The silastic body around the electrode lead 401 acts as an impact reinforcement element for resisting effects of an external impact. In other embodiments, such an impact reinforcement element may be made of an appropriate polymer and/or metallic material.

FIG. 5A-D shows example photographs of impact reinforcement elements in the form of helical springs according to embodiments of the present invention. Helical spring 501 in FIG. 5A is made from round wire, whereas the helical spring 502 if formed from ribbon wire. Characteristics such as the wire material, size, spring diameter, and spring pitch can be controlled to achieve desired mechanical properties. The impact reinforcement around a portion of the electrode lead may be embedded in the main electrode body (as shown, for example, in FIGS. 5 B and C), or it may be external to it (for example, as in FIG. 5 D).

Figure 6A:
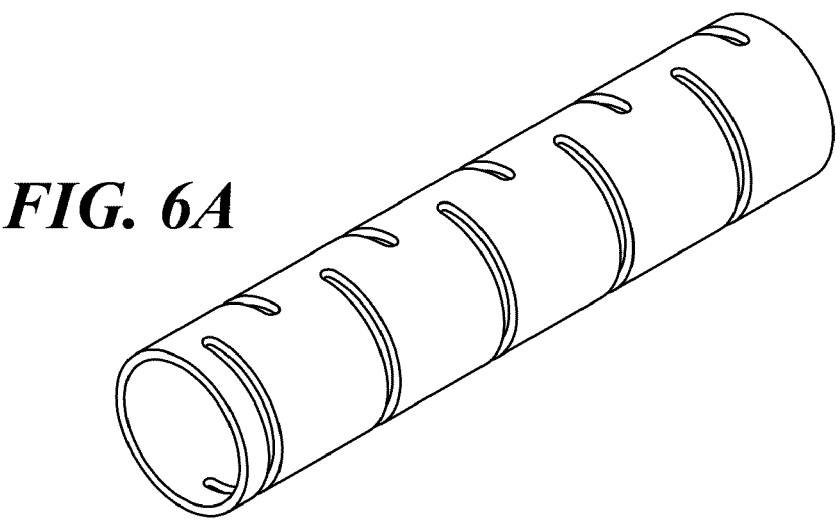
FIG. 6 A-C shows examples of impact reinforcement elements in the form of tubular structures with different patterns of slits according to various specific embodiments of the present invention.
Figure 6B:
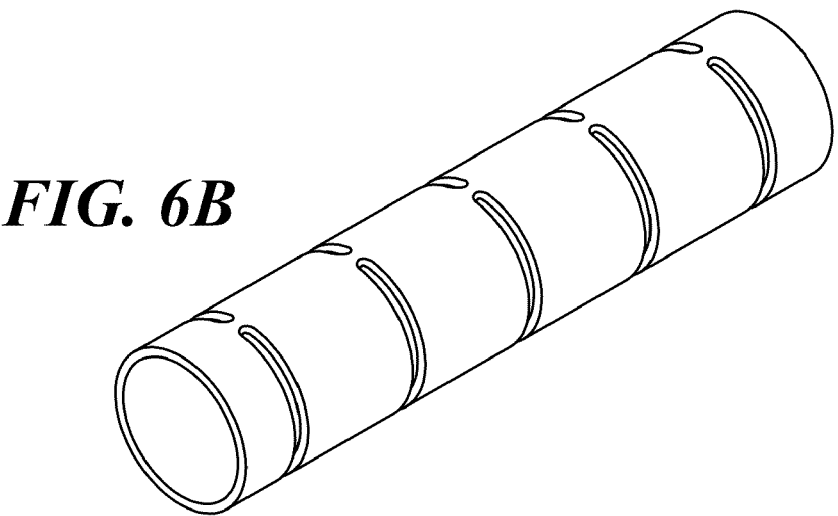
Figure 6C:
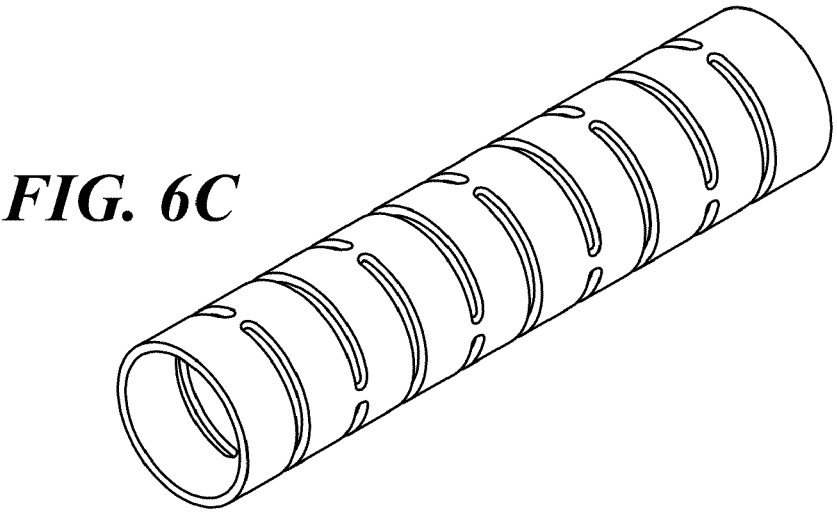

FIG. 6 A-C shows examples of impact reinforcement elements in the form of tubular structures with different patterns of slits according to various specific embodiments of the present invention. The number, size, and relative arrangement of the slits may be controlled to achieve desired mechanical properties such as bend radius and direction and impact resistance.

Although various exemplary embodiments of the invention have been disclosed, it should be apparent to those skilled in the art that various changes and modifications can be made which will achieve some of the advantages of the invention without departing from the true scope of the invention.

What is claimed is:

1. A cochlear implant electrode comprising:
    an extra-cochlear electrode lead containing a plurality of electrode wires for carrying electrical stimulation signals from an implant housing to a cochleostomy opening; and an intra-cochlear electrode array containing the plurality of electrode wires and passing from the cochleostomy opening into a cochlea scala and terminating in a plurality of electrode contacts for applying the electrical stimulation signals to target neural tissue;

wherein one or more of the electrode wires in the electrode lead has an associated periodic waveform lead shape and one or more of the electrode wires in the electrode array has an associated periodic waveform array shape.

2. An electrode according to claim 1, wherein the lead shape and the array shape each have an associated periodic amplitude, and wherein the array shape periodic amplitude differs from the lead shape periodic amplitude.

3. An electrode according to claim 1, wherein at least one of the shapes includes a smoothly varying wave that repeats.

4. An electrode according to claim 1, wherein at least one of the shapes includes a sequence of coiled loops.

5. An electrode according to claim 1, wherein the one or more electrode wires in the electrode lead includes a portion without the periodic waveform lead shape.

6. An electrode according to claim 5, wherein the one or more electrode wires in the electrode lead includes a portion having the periodic waveform lead shape on each side of the portion without the periodic recurring lead shape.

7. An electrode according to claim 1, wherein the one or more electrode wires in the electrode array includes a portion without the periodic waveform array shape.

8. An electrode according to claim 7, wherein the one or more electrode wires in the electrode array includes a portion having the periodic waveform array shape on each side of the portion without the periodic waveform array shape.

9. An electrode according to claim 7, wherein the portion of the one or more electrode wires in the electrode array without the periodic waveform array shape is rigid for pushing the electrode array into the cochlea scala.

10. An electrode according to claim 1, wherein the one or more electrode wires in the electrode lead having the lead shape include a portion having a different second periodic waveform lead shape.

11. An electrode according to claim 1, wherein the one or more electrode wires in the electrode array have a plurality of different array shapes.

12. An electrode according to claim 1, further comprising:
an impact reinforcement element around a portion of the electrode lead for resisting effects of an external impact.

13. An electrode according to claim 12, wherein the impact reinforcement element is a polymer material.

14. An electrode according to claim 12, wherein the impact reinforcement element is a metallic material.

15. An electrode according to claim 1, wherein the electrode wires have an elliptical cross-section.

* * * * *